United States Patent [19]

Yates et al.

[11] Patent Number: 5,735,848

[45] Date of Patent: *Apr. 7, 1998

[54] ELECTROSURGICAL STAPLING DEVICE

[75] Inventors: David C. Yates, West Chester; Jesse J. Kuhns, Cincinnati; Steven H. Mersch, Germantown, all of Ohio

[73] Assignee: Ethicon, Inc., Cincinnati, Ohio

[*] Notice: The term of this patent shall not extend beyond the expiration date of Pat. No. 5,403,312.

[21] Appl. No.: 425,705

[22] Filed: Apr. 20, 1995

Related U.S. Application Data

[63] Continuation of Ser. No. 96,154, Jul. 22, 1993, abandoned.

[51] Int. Cl.⁶ .................................................. A61B 17/36
[52] U.S. Cl. ........................... 606/48; 606/50; 606/142; 227/175.1
[58] Field of Search .............................. 606/40, 41, 42, 606/45–52, 142, 143, 205–209; 227/175.1

[56] References Cited

U.S. PATENT DOCUMENTS

| | | |
|---|---|---|
| 2,031,682 | 2/1936 | Wappler et al. . |
| 4,608,981 | 9/1986 | Rothfuss et al. . |
| 4,633,874 | 1/1987 | Chow et al. . |
| 4,655,216 | 4/1987 | Tischer . |
| 4,671,274 | 6/1987 | Sorochenko . |
| 4,985,030 | 1/1991 | Melzer et al. . |
| 5,057,107 | 10/1991 | Parins et al. . |
| 5,085,659 | 2/1992 | Rydell . |
| 5,104,025 | 4/1992 | Main et al. . |
| 5,151,102 | 9/1992 | Kamiyama et al. ............... 606/51 |
| 5,201,900 | 4/1993 | Nardella . |
| 5,389,098 | 2/1995 | Tsuruta et al. ................... 606/41 |
| 5,403,312 | 4/1995 | Yates et al. ...................... 606/50 |
| 5,443,463 | 8/1995 | Stern et al. ....................... 606/51 |
| 5,496,312 | 3/1996 | Klicek ............................... 606/34 |

FOREIGN PATENT DOCUMENTS

| | | |
|---|---|---|
| 0 517 244 | 12/1992 | European Pat. Off. . |
| 0 518 230 | 12/1992 | European Pat. Off. . |
| 1459659 | 9/1986 | U.S.S.R. . |
| WO 93/08754 | 5/1993 | WIPO . |

OTHER PUBLICATIONS

Automatically Controlled Bipolar Electrocoagulation—"COA–COMP", Neurosurg, Rev. (1984) 187–190 B. Vallfors and B. Bergdahl.

Primary Examiner—Michael Peffley

[57] ABSTRACT

An surgical stapling instrument is provided which uses a thermogenic energy preferably bipolar radiofrequency energy for cauterization and/or welding tissue. The instrument compresses tissue between one pole of a bipolar energy sources contained on a first interfacing surface and a second pole of a bipolar energy source contained on a second interfacing surface. Staples and thermogenic energy are applied to the compressed tissue. In a preferred embodiment a cutting element for cutting tissue is incorporated into the instrument.

28 Claims, 8 Drawing Sheets

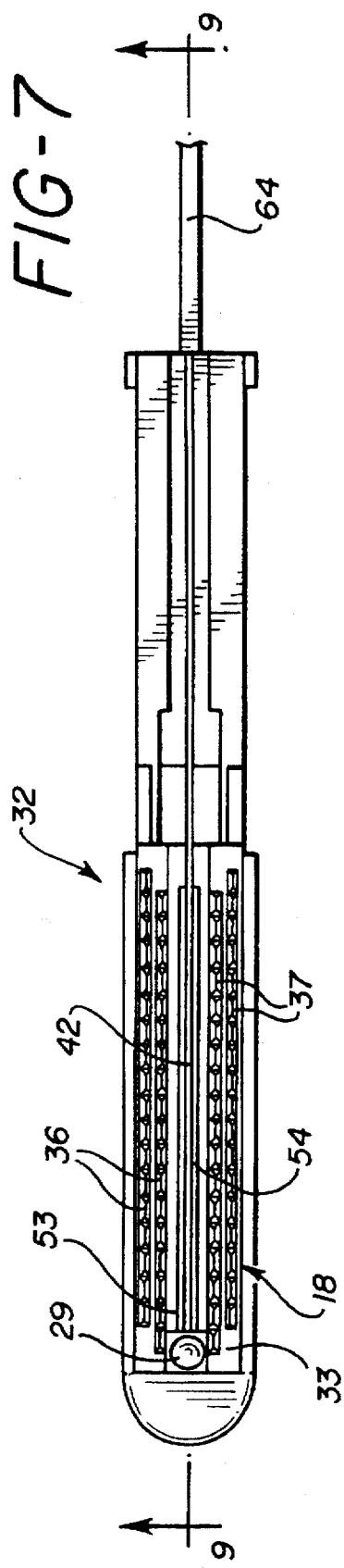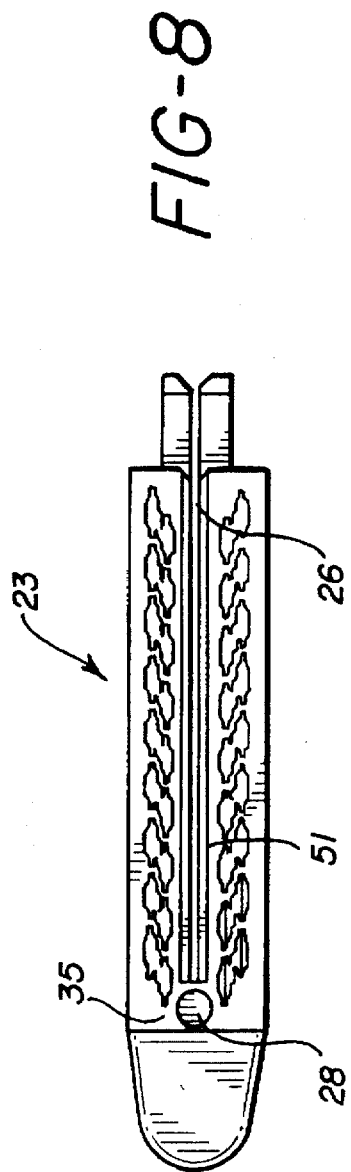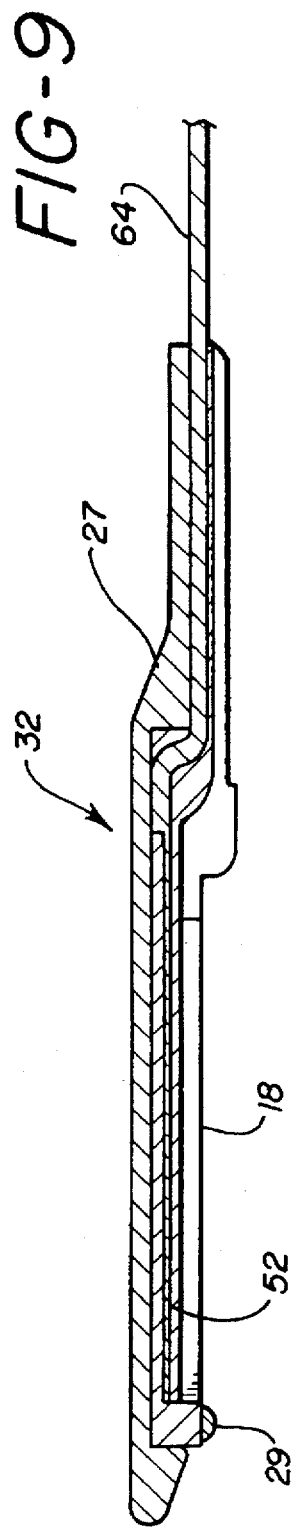

ELECTROSURGICAL STAPLING DEVICE

This is a continuation of application Ser. No. 08/096,154, filed Jul. 22, 1993 (now abandoned).

FIELD OF THE INVENTION

This invention relates to an instrument which uses a stapling means and a thermogenic energy for cauterization, coagulation and/or tissue joining or welding in the performance of surgical procedures.

BACKGROUND OF THE INVENTION

Surgical procedures requiring cutting of tissue can cause bleeding at the site of the cutting. Before surgeons had the means to control bleeding many surgical procedures were quite difficult to perform because of excessive blood loss. Hemostasis is even more crucial in endoscopic or laparoscopic surgery where if the bleeding is not kept under control, the laparoscopy must be abandoned and the patient's body cut to perform open surgery so that inaccessible bleeding may be controlled.

Thus, various techniques have been adapted to control bleeding with varying degrees of success such as, for example, suturing, applying clips to blood vessels, and stapling, as well as monopolar and bipolar electrocautery and other thermogenic techniques. Advances in tissue joining, tissue repair and wound closure also have permitted surgical procedures previously not possible or too risky.

Initially, suturing was one of the primary means for providing hemostasis and joining tissue. Before other hemostatic and tissue repair means were introduced, surgeons had to spend a great deal of time sewing the tissue of patients back together.

Surgical clips were introduced as a means to close off blood vessels, particularly when cutting highly vascularized tissue. Application of surgical clips, however, can be cumbersome in certain procedures. The vessels must be identified. Then a clip must be individually applied on both sides of the intended cut of each identified vessel. Also, it may be difficult to find some vessels, particularly where the vessel is surrounded by fatty tissue.

Surgical staplers have been effective in decreasing the amount of time it takes to fasten tissue together. There are various types of surgical staplers. Staplers have been used for tissue joining, and to provide hemostasis in conjunction with tissue cutting. Such devices include, for example, linear and circular cutting and stapling instruments. Typically, a linear cutter has parallel rows of staples with a slot for a cutting means to travel between the rows of staples. This type of surgical stapler secures tissue for improved cutting, joins layers of tissue, and provides hemostasis by applying parallel rows of staples to layers of surrounding tissue as the cutting means cuts between the parallel rows. These types of cutting and stapling devices have been used successfully in procedures involving fleshy tissue such as muscle or bowel, particularly in bowel resection procedures. Circular cutting and stapling devices have successfully been used, for example, in anastomotic procedures where a lumen is rejoined. However, tissue may not provide uniform thickness for stapling and thus, particularly in thicker tissue, the staples may not fully compress blood vessels. Also, because of the fragility of some tissues it may not be desirable to fully compress the tissue with staples to obtain complete hemostasis.

Thus, it is desirable to provide improved hemostasis with surgical stapling.

Therefore it is an object of the invention to provide an improved stapling device which uses a thermogenic energy, preferably bipolar energy, to assist in providing hemostasis, tissue joining or welding. It is a further object to provide such a device which may be used on an area or length of relatively thicker tissue.

It is another object of the invention to provide a bipolar electrocautery device having elongated or bar electrodes.

It is also an object to provide a cutting and stapling device with an electrocautery means for tissue welding or cauterization lateral to a cutting line or path.

SUMMARY OF THE INVENTION

These and other objects of the invention are described in an electrosurgical stapling device having an end effector with opposing interfacing surfaces associated with jaws for engaging and stapling tissue therebetween, and two electrically opposite poles located on the opposing surfaces.

An electrosurgical instrument of one embodiment compresses tissue in a compression zone between a first interfacing surface and a second interfacing surface and applies electrical energy through the compression zone. The first interfacing surface is comprised of: a first pole of a bipolar energy source, which interfaces with the compressed tissue in the compression zone; and a second pole located on the opposite interfacing surface.

In a one embodiment, the compression zone is an area defined by a compression ridge on one of the interfacing surfaces which compresses the tissue against the other interfacing surface. Also, there may also be a compression ridge on both interfacing surfaces. A coagulation zone is defined by the heat dissipated through the engaged tissue from the current traveling through the tissue between the first and second poles.

It is believed that the tissue compression normalizes tissue impedance by reducing structural differences in tissue which can cause impedance differences. Compression also stops significant blood flow and squeezes out blood which acts as a heat sink, particularly when flowing through blood vessels. Thus, compression optimizes delivery of energy to tissue in part by enabling the rate of energy delivery to exceed the rate of dissipation due to blood flow. The arrangement of the electrodes is important to ensure that the current passing between the two electrodes passes though the compression zone.

Compression by the end effector is preferably balanced against causing unacceptable tissue damage from excessive compression. A gap, between interfacing surfaces defining the compression zone, can be varied depending on the intended application of the instrument or the thickness of the tissue on which the instrument is used.

In some procedures, the tissue may be easily damaged under compression, not only by the end effector, but also by the staples. For example, lung tissue may exhibit such fragility. Thus, with such tissue types it is preferable that tissue compression by engaging tissue with the end effector or stapling be kept at a minimum. Under such circumstances stapling may not fully compress the blood vessels at which hemostasis is desired. The present invention is particularly suitable for use under such conditions. Also the device of the present invention is suitable for use with thicker tissue, for example, a thick mesentery tissue, typically about 2–5 mm thick. With this type of tissue, a gap between the jaws of about 1.5 mm to 2 mm would be preferred.

A preferred embodiment of the invention provides first and second poles which overlap each other, i.e., so that some portion of the electrically conductive surfaces of the poles orthogonally intersects a plane common to the electrodes of both poles. This embodiment is particularly useful for controlling the zone of coagulation and tissue impedances, especially in thick or less compressed tissue which may present higher or less uniform tissue impedances.

The present invention also provides a device capable of coagulating a line or path of tissue lateral to a cut line or a cutting path with a stapling means provided on one or both sides of the cut line or cutting path. In one embodiment, the first pole comprises an elongated electrode. The elongated electrode along with the adjacent insulator form a ridge to compress the tissue to be cauterized.

In another embodiment, the coagulation is completed prior to any mechanical cutting, i.e., actuation of the cutting means. An indicator means may be used to communicate to the user that the tissue has been cauterized to a desired or predetermined degree. Once tissue is cauterized, the cutting means may be actuated to cut between the parallel bars while the rows of staples are applied to the tissue. Of course, cutting may occur at anytime either before, during or after cauterization or welding.

In another embodiment, the hemostatic device is incorporated into a linear cutter similar to a linear cutting mechanical stapler. In this embodiment the hemostatic device comprises two parallel and joined elongated electrode bars which form one pole, and a slot for a cutting means to travel between the bars. Optionally, one or more rows of staples may be provided on each side of the slot and bars to provide additional hemostasis. In operation, tissue is clamped between two jaws. Electrical energy preferably radio frequency energy is applied to the compressed tissue to cauterize the blood vessels along the two parallel bars.

Similarly another embodiment provides a tissue welding and cauterizing cutting device similar to an intraluminal stapler. Preferably, the poles are formed in two concentric circles and oppose each other on the cartridge and anvil interfacing surfaces.

Another embodiment provides a means for detecting abnormal impedances or other electrical parameters which are out of a predetermined range. For example, the means for detecting may be used to indicate when the instrument has been applied to tissue exhibiting impedances out of range for anticipated good coagulation. It may also be used for detecting other instrument abnormalities. It is possible to detect the abnormal condition, for example, by using comparisons of normal ranges of initial tissue impedances in the interface electronics. This could be sensed in the first few milliseconds of the application of RF energy and would not present a significant therapeutic dose of energy. A warning mechanism may be used to warn the user when the impedance is out of range. Upon repositioning of the instrument, the same measurement criteria would apply and if the tissue impedance was again out of range, the user would again be warned. This process would continue until the normal impedance range was satisfied and good coagulation could be anticipated.

Although the preferred embodiment of the invention uses bipolar energy as a means for cauterizing tissue other thermogenic means may be used as well, for example laser energy, ultrasonic energy or other tissue heating means.

These and other objects of the invention will be better understood from the following attached Detailed Description of the Drawings, when taken in conjunction with the Detailed Description of the Invention.

DETAILED DESCRIPTION OF THE DRAWINGS

FIG. 7 is a bottom isolated view of the anvil jaw of the instrument of FIG. 1;

FIG. 8 is a top isolated view of a cartridge of the instrument of FIG. 1;

FIG. 9 is a side cross sectional view of the jaw of FIG. 7 along the line 9—9;

DETAILED DESCRIPTION OF THE PREFERRED EMBODIMENTS

Figure 1:
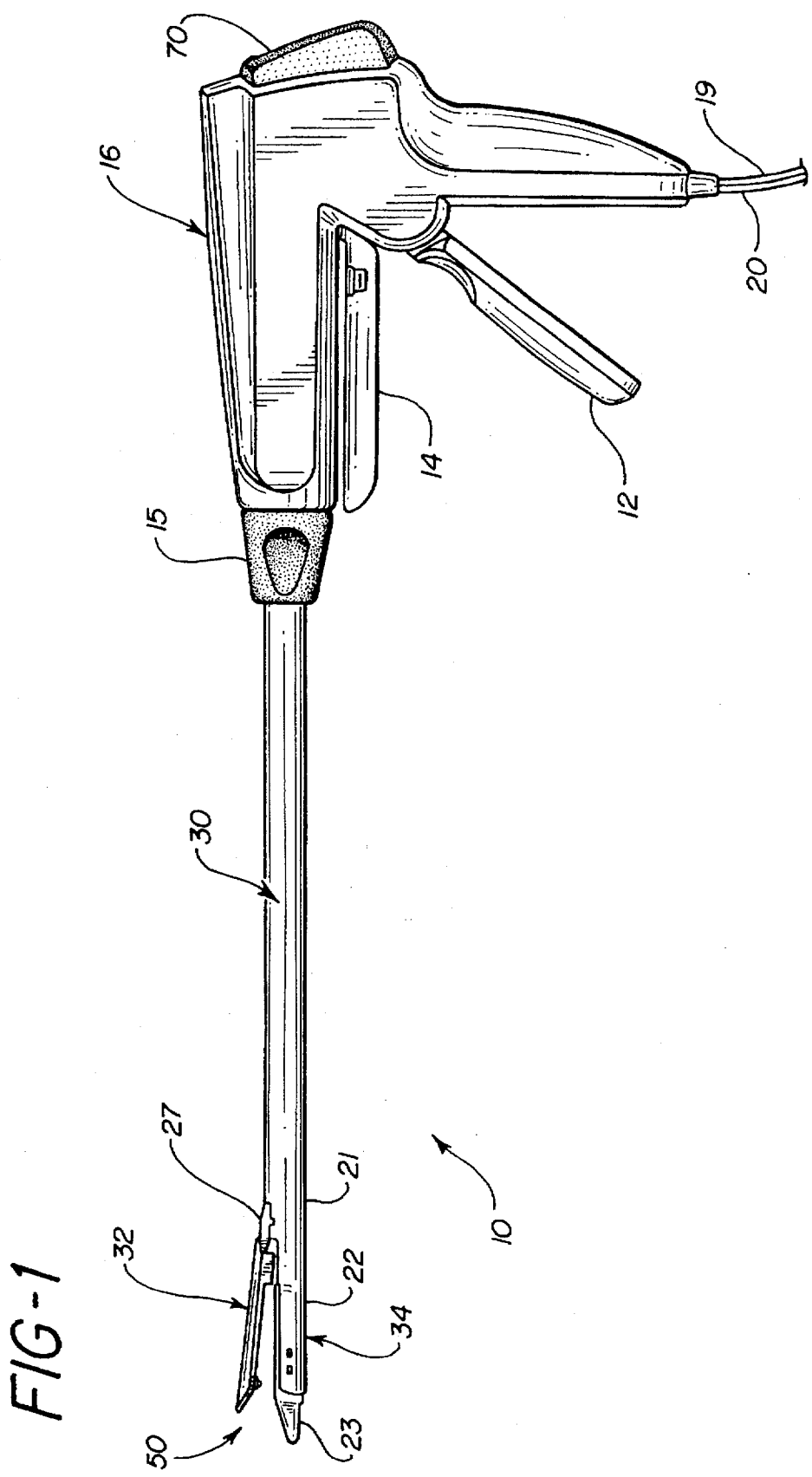
FIG. 1 is a side elevational view of an endoscopic electrocautery linear stapling and cutting instrument of one embodiment of the present invention.
Figure 2:
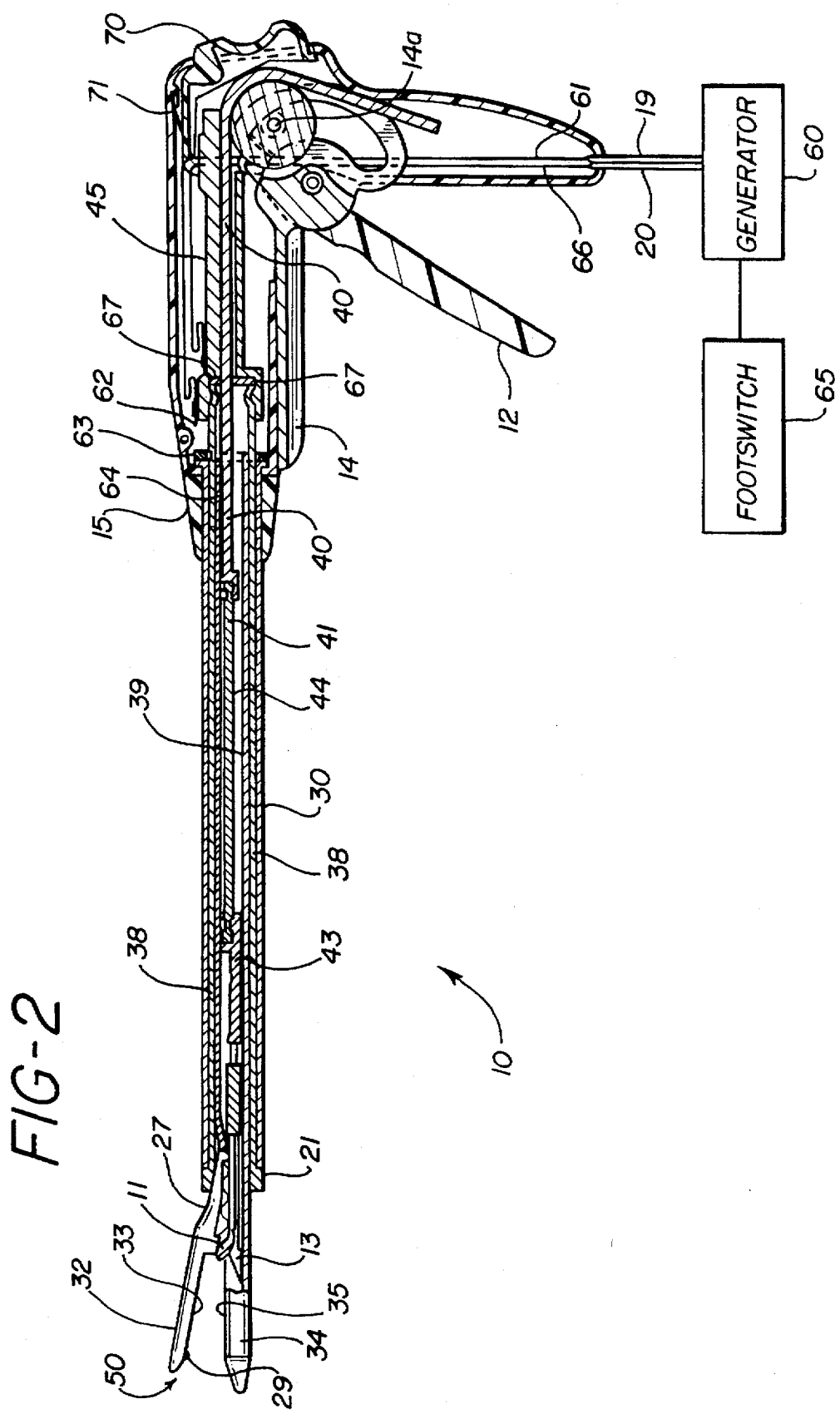
FIG. 2 is a side cross sectional view of the instrument of FIG. 1.
Figure 3:
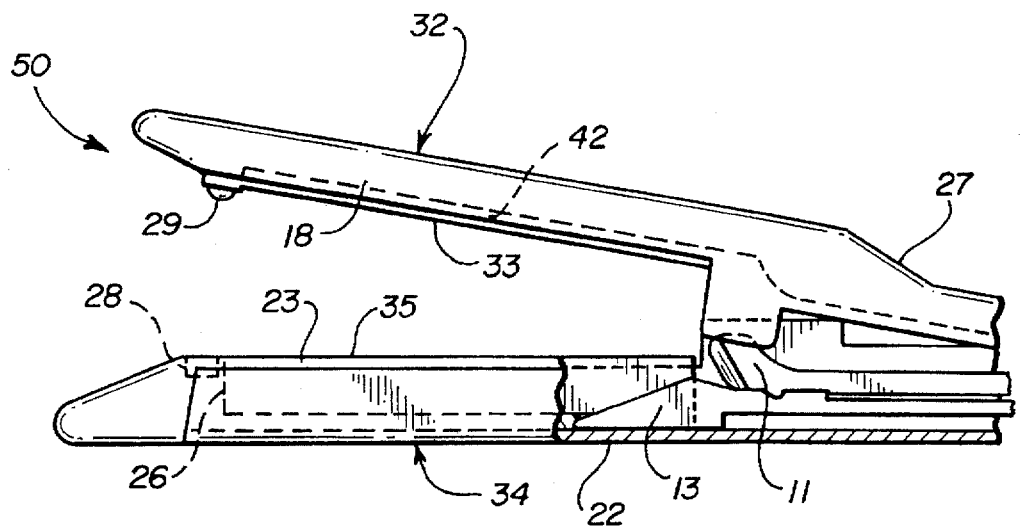
FIG. 3 is a partial cross sectional view of the distal end of the instrument of FIG. 1 in an open position.
Figure 4:
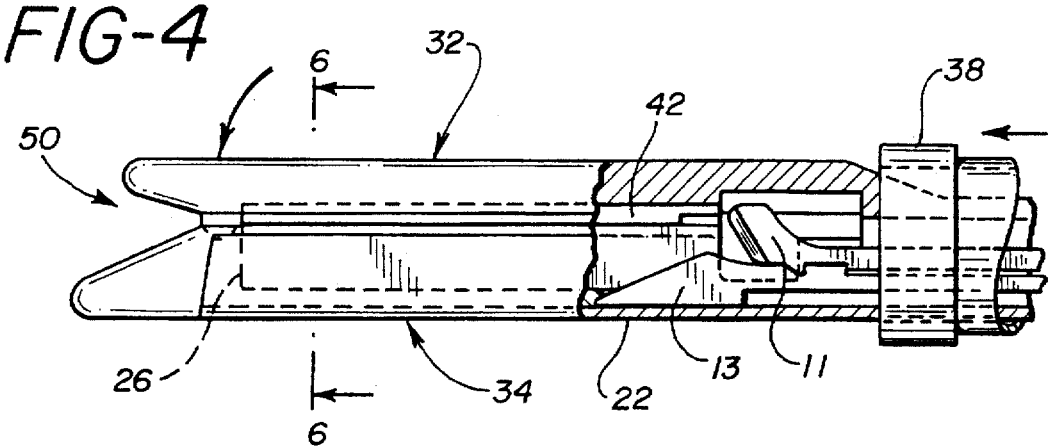
FIG. 4 is a partial cross sectional view of the distal end of the instrument of FIG. 1 in a closed, unfired position.
Figure 5:
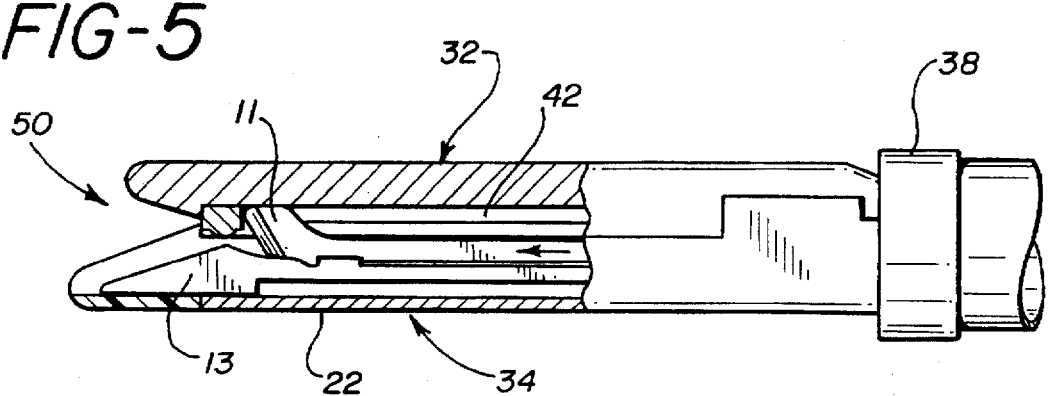
FIG. 5 is a partial cross sectional view of the distal end of the instrument of FIG. 1 in a closed, fired position.

Referring now to FIGS. 1–9, there is illustrated a preferred embodiment of the present invention. An endoscopic electrocautery linear cutting and stapling instrument 10 is shown having a body 16 coupled to a shaft 30 with a lumen extending therethrough and an end effector 50 extending from the distal end 21 of the shaft 30. The shaft 30 is formed of an insulative material and has an electrically conductive sheath 38 extending through its lumen. A channel 39 extending through the sheath 38 guides co-axial movement of a driver means 44 within the channel 39. In this particular embodiment, the driver means 44 includes a firing trigger 14 associated with the body 16, coupled to a flexible firing rod 40 coupled to a driving rod 41, coupled to a block 43. The block 43 is coupled to a cutting means 11 and a staple driving wedge 13, which the driving means 44 advances by way of the block 43 into the end effector 50.

The end effector 50 comprises two interfacing jaw members 32, 34. The end effector 50 is secured by way of jaw member 34 to the channel 39. The jaw member 32 is movably secured to jaw member 34. The body 16 has a clamping trigger 12 for closing the jaws 32, 34 which longitudinally advances a close rack 45 coupled to the proximal end of the sheath 38. The close rack 45 advances the sheath 38 co-axially through the shaft 30. The sheath 38 advances over a camming surface 27 of jaw 32 to close the jaws 32 and 34 onto tissue situated between the jaws. As described in more detail below, the close rack 45 also acts as a switch to close the circuit which communicates electrical energy to the end effector 50.

Figure 6:
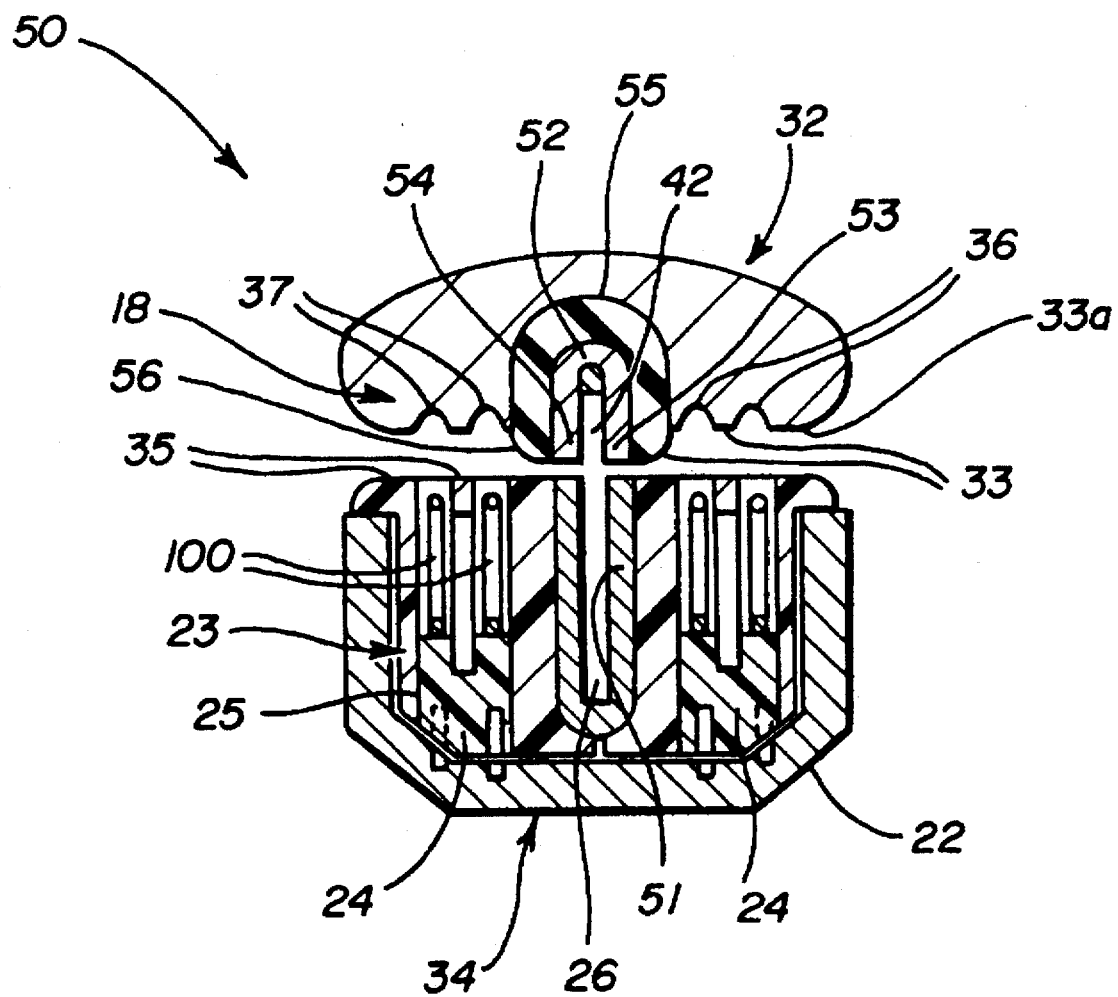
FIG. 6 is a front cross sectional view of the distal end of the instrument of FIG. 4 taken along the line 6—6.

Referring now to FIGS. 3–9 an enlargement of the end effector 50 of the instrument 10 is illustrated. The jaw members 32 and 34 are shown in an unclamped position in FIG. 3, in a clamped, unfired position in FIG. 4 and in a clamped, fired position in FIG. 5. Jaw member 32 comprises an anvil 18, a U-shaped first pole 52 extending longitudinally with respect to the jaw 32, and a U-shaped insulating material 55 surrounding the outside of the first pole 52. Jaw member 32 has an inner surface 33 which faces an inner surface 35 of jaw 34. The inner surface 33 includes first pole 52 which comprises two electrically communicating electrode bars 53, 54 comprised of stainless steel, extending substantially along the length of the inner surface 33. The bars 53, 54 are separated by a knife channel 42 extending longitudinally through the first pole's center to form its U-shape. The surface of the bars are formed in flat strips to provide more surface area contact with tissue. Two series of pockets 36, 37 located on anvil 18, for receiving staple ends, extend along the inner surface 33, lateral to and outside of bars 53, 54 respectively. The electrode bars 53, 54 and the insulating material 55 form a ridge 56 extending out relative to the anvil portion 33a of the inner surface 33 (FIG. 6). The anvil 18 is formed of an electrically non-conductive material. A second pole 51 is located on jaw 34 opposite electrode bars 53, 54.

Jaw member 34 comprises a cartridge channel 22 and a cartridge 23. The cartridge 23 includes a track 25 for the wedge 13, knife channel 26 extending longitudinally through the center of the cartridge 23, a series of drivers 24 extending into track 25 and staples 100 arranged in two sets of parallel double rows. When tissue is engaged between the jaws 32, 34, the driver means 44 may be actuated or fired using trigger 14 to advance the cutting means 11 and wedge 13 through the engaged tissue to staple and cut the tissue. When the firing mechanism 14 is actuated, the wedge 13 is advanced through the track 25 causing the drivers 24 to displace towards the staples 100, thereby driving the staples 100 through tissue and into anvil pockets 36, 37.

A gap pin 29 located on the inner surface 33 towards the tip of the anvil 18 fits into a gap 28 is formed on the inner surface 35 of the cartridge 23. The gap 28 and gap pin 29 serve to align the knife channels 42, 26 with each other, and for the staples 100 to line up with the pockets 36, 37.

A knob 15 located on the distal end of the body 16 rotates the shaft 30, sheath 38, channel 39 and end effector 50 which are directly or indirectly coupled to the knob 15 so that the knob 15 may be used for rotational placement of the end effector jaws 32,34.

Bipolar energy is supplied to the end effector 50 from an electrosurgical generator 60 through wires 19, 20 extending into the body 16 of the instrument. The generator 60 is user controlled by way of a footswitch 65.

Wire 19 which provides electrical current to the first pole energy, is coupled through a wire or other electrical contact means 61 to electrical contact 62 located on the distal end of close rack 45. Wire 20 which carries the current of the opposite pole, is coupled through a wire or other electrical contact means 66 to a disc contact 67 located at the distal end of the close rack 45 and electrically isolated from contact 62.

A disc contact 63, associated with the first pole 52, located at the distal end of the body 16 is in electrical communication with a wire or other contact means 64. Contact means 64 extends through channel 39 to end effector jaw 32 where it contacts first pole 52. The disc contact 63 permits the knob 15 to rotate while contact is maintained between the disc contact 63 and the contact means 64. The contact means 64 is electrically insulated from the sheath 38.

When the clamping trigger 12 is actuated, the close rack 45 moves distally so that the contact 62 associated with the first pole comes in electrical communication with the disc contact 63 and the disc contact 67 associated with the second pole 51 comes in electrical contact with the electrically conductive sheath 38. The sheath 38 moves over the electrically non-conducting camming surface 27 and is in contact with the electrically conducting cartridge channel 22. The cartridge channel 22 is in electrical communication with second pole 51, electrically opposite of the first pole. Thus the electrical circuit is closed when and only when the clamping trigger 12 is closed.

In operation, the end effector 50 of the instrument is located at a tissue site where tissue is to be cut. The jaw members 32, 34 are opened by pressing a release button 70 which releases a button spring 71 and permits the close rack 45 to move proximally. Tissue is then placed between the interfacing inner surfaces 33, 35 respectively of the jaw members 32, 34. The clamping trigger 12 is squeezed to cause the sheath 38 to move over the camming surface 27 and thereby close the jaws 32, 34 and simultaneously close the electrical circuit as described above. The gap spacing pin 29 causes the anvil 18 to be held roughly parallel to the cartridge 23. The electrode bars 53, 54 and the insulating material 55, which together form the ridge 56, compress the tissue against the inner surface 35 of jaw member 34 on which return electrode 51 is contained. A gap of about between 1.5 mm and 2.0 mm exists between jaw members in the compression zone. A user then applies RF energy from the generator 60 using the footswitch 65 or other switch. Current flows through the compressed tissue between the second pole 51 and the bars 53, 54 of the first pole 52.

Preferably the bipolar energy source is a low impedance source providing radio frequency energy from about 300 kHz to 3 MHZ. Preferably, the current delivered to the tissue is from 0.1 to 1.5 amps and the voltage is from 30 to 200 volts RMS.

An audible, visible, tactile, or other feedback system may be used to indicate when sufficient cauterization has occurred at which point the RF energy may be turned off. An example of such a feedback system is described below. After the RF energy is turned off, the cutting means 11 is advanced and the staples 100 are fired using the firing trigger 14. Firing is accomplished by rotating the firing trigger 14 acting as a lever arm about pivot 14a. The driver means 44 advances the cutting means 11 and wedge 13. The cutting means 11 cuts the tissue in between the bars 53, 54 where the tissue has been cauterized. Thus, the cut line is lateral to the coagulation lines formed by the bar electrodes. The wedge 13 simultaneously advances the drivers 24 into the staples 100 causing the staples 100 to fire through tissue and into the pockets 36, 37 of the anvil 18. Staples 100 are applied in two longitudinal double rows on each side of the cutting means 11 as the cutting means cuts the tissue.

Operation of linear staplers are known in the art and are discussed, for example, in U.S. Pat. Nos. 4,608,981, 4,633, 874, and U.S. application Ser. No. 07/917,636 incorporated herein by reference.

In one embodiment the cartridge provides multifire stapling capabilities by replacing the double row of staples with a single row. In the laparoscopic stapling and cutting devices presently in use, a single shot replaceable cartridge is used. In order to provide better hemostasis, this type of stapler was designed to provide a double row of staples for each parallel row. Because of the size of the space necessary to contain the double row of staples, a refireable cartridge with stacked staples has not been preferred because of the additional space required for stacking staples. In the multifire stapling embodiment a single row of staples is used. Using a single row of staples permits stacking of staples in the space previously occupied by the second row of staples, providing multifire capabilities. In a further embodiment, no staples are required and the electrical current provides the necessary hemostasis.

A preferred embodiment of the present invention includes a feedback system designed to indicate when a desired or predetermined degree of coagulation has occurred. This is particularly useful where the coagulation zone is not visible to the user. In a particular embodiment, the feedback system measures electrical parameters of the system which indicate coagulation level.

The feedback system may also determine tissue characteristics at or near a coagulation zone which indicate degree of coagulation. The electrical impedance of the tissue to which the electrical energy is applied may also be used to indicate coagulation. Generally, as energy is applied to the tissue, the impedance will initially decrease and then rise as coagulation occurs. An example of the relationship between electrical tissue impedance over time and coagulation is described in Vaellfors, Bertil and Bergdahl, Bjoern "Automatically controlled Bipolar Electrocoagulation," Neurosurg. Rev. p. 187–190 (1984) incorporated herein by reference. Also as desiccation occurs impedance increases. Tissue carbonization and or sticking to instrument as a result of over application of high voltage may be prevented using a feedback system based on tissue impedance characteristics. Other examples of tissue characteristics which may indicate coagulation include temperature and light reflectance.

Figure 10:
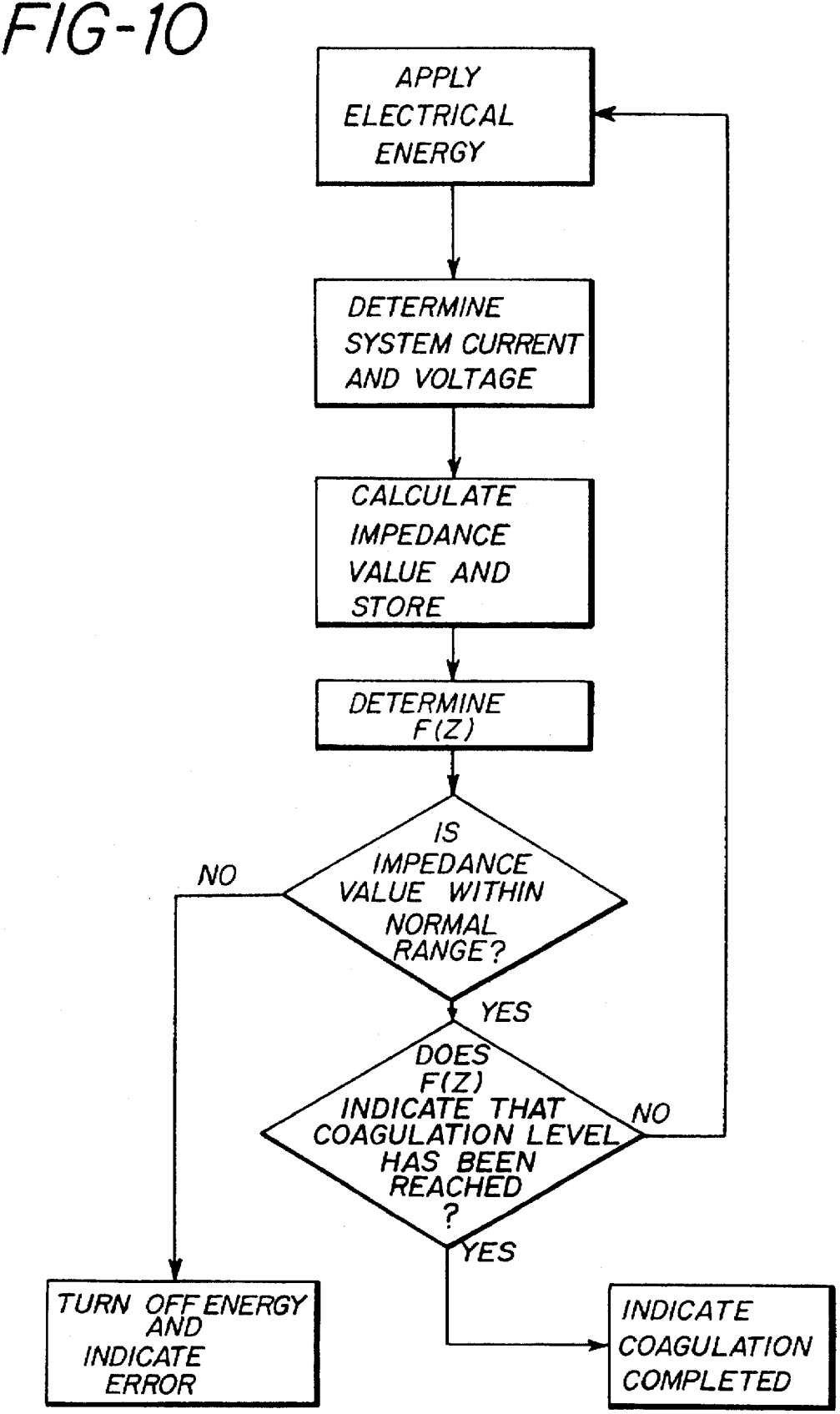
FIG. 10 is a flow chart illustrating a feedback system of the present invention.

Referring to FIG. 10, a flow chart illustrates a feedback system which is implemented in a preferred embodiment of the present invention. First, energy is applied to the tissue. Then the system current and voltage applied to the tissue is determined. The impedance value is calculated and stored. Based on a function of the impedance, for example, which may include the impedance, the change in impedance, and/or the rate of change in impedance, it is determined whether desired coagulation has occurred. If coagulation has occurred to a desired degree, an indication means indicates that the energy should be turned off. Such an indication means may include a visible light or an audible sound. The feedback means may also control the generator and turn the energy off at a certain impedance level. An alternative embodiment provides a continuous audible sound in which the tone varies depending on the impedance level. An additional feature provides an error indication means for indicating an error or instrument malfunction when the impedance is in below a normal minimum and/or above a maximum range.

Figure 11:
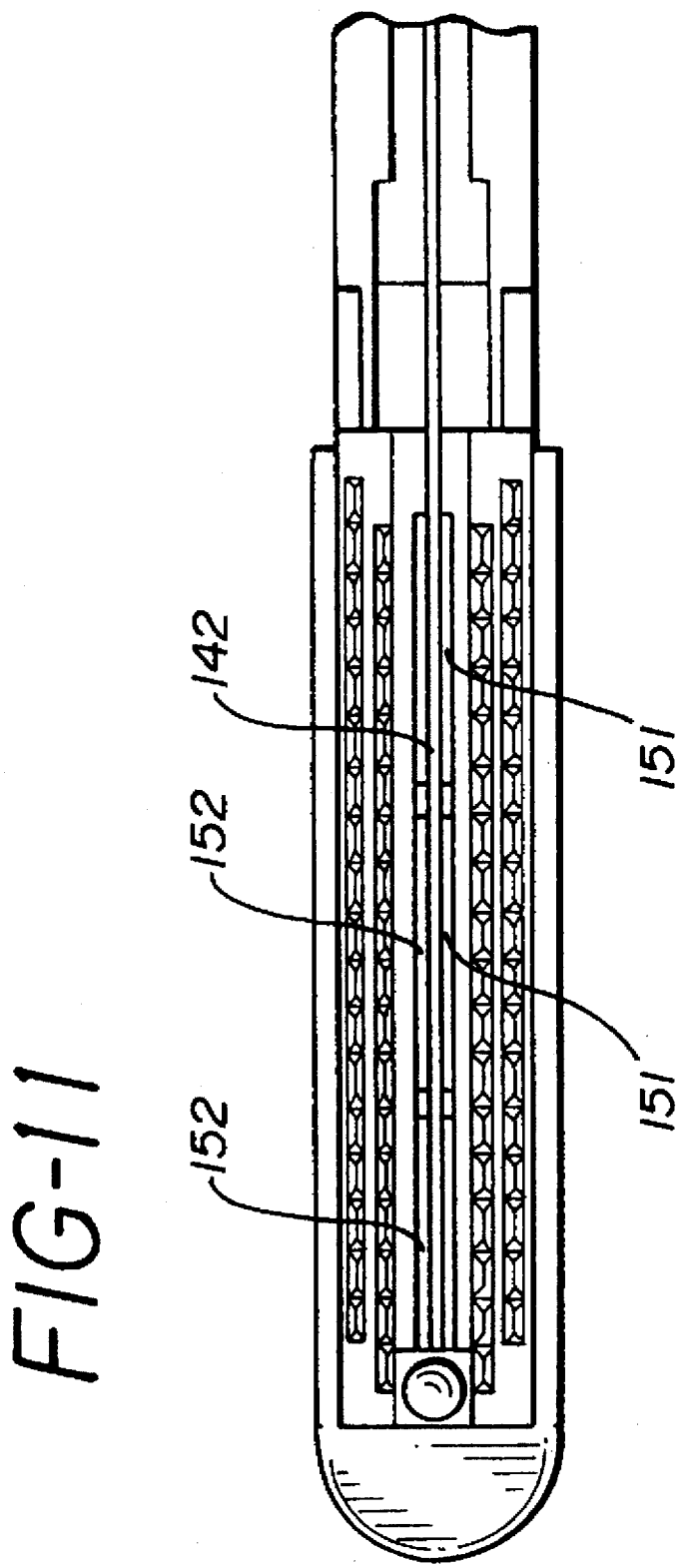
FIG. 11 is a bottom isolated view of the anvil of another embodiment of the present invention.

FIG. 11 illustrates an alternative embodiment. The poles 151, 152 are arranged similar to as in FIG. 6, but with each pole as a series of electrically connected electrodes staggered along the length of the knife channel with insulating material in between staggered electrodes. Knife channel 142 separates poles 151 and 152 into two elongated series of electrodes.

Figure 12:
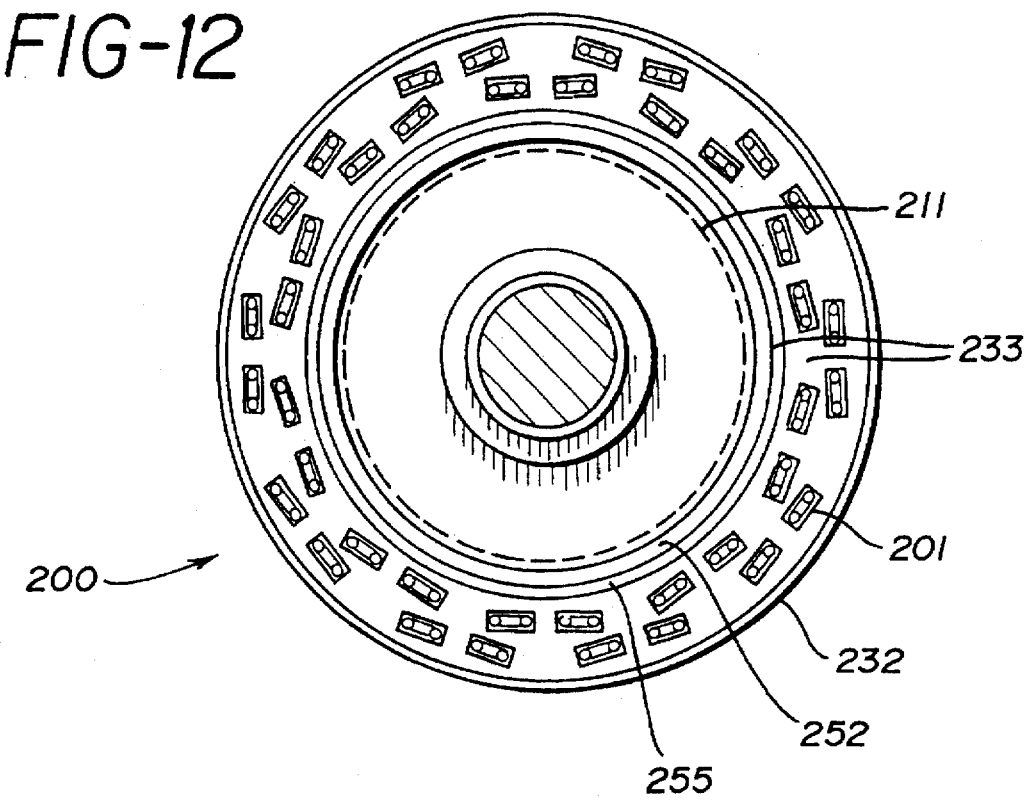
FIG. 12 is a top view of a cartridge of a circular cutter of the present invention.
Figure 13:
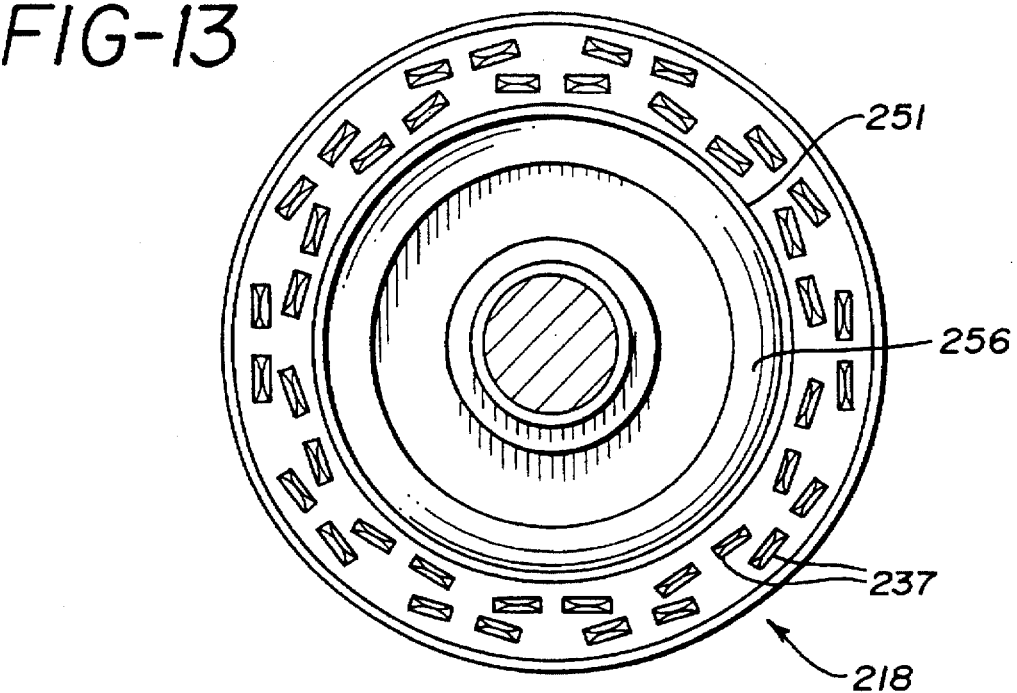
FIG. 13 is a bottom view of the anvil of a circular cutter of the present invention.

FIGS. 12 and 13 illustrate a circular cutter of the present invention with stapling means. FIG. 12 illustrates the stapler cartridge 200 with an interfacing surface 233. A double row of staple apertures 201 through which staples are driven into tissue are staggered about the outer circumference of the surface 232. A first pole 252 encircles the inner circumference of the surface 233. A circular cutting knife 211 is recessed within the cartridge 200 radially inward from the inner circumference of the surface 233.

FIG. 13 illustrates an anvil 218 having a second pole 251 electrically opposite of the first pole 252. An insulator 255 on the cartridge 200 electrically isolates the first pole 252 from the second pole 251. The anvil 218 includes pockets 237 for receiving staples and a compression ridge 256 for compressing tissue against the first pole 252 and insulator 255 of the cartridge. The circular cutter is operated similarly to the circular stapler described in U.S. Pat. No. 5,104,025 incorporated herein by reference. Prior to stapling and cutting however, tissue welding electrical current may be delivered between the first pole 252 and the second pole 251 to tissue.

In an alternative embodiment, the circular cutter may be used without staples. Electrical current is delivered through the poles to weld and coagulate tissue, then the knife may be advanced to cut tissue in a procedure such as an anastomosis.

Several variations of this invention has been described in connection with specific embodiments involving endoscopic cutting and stapling. Naturally, the invention may be used in numerous applications where hemostasis in desired. Accordingly, will be understood by those skilled in the art that various changes and modifications may be made in the invention without departing from its scope, which is defined by the following claims and their equivalents.

What is claimed is:

1. An electrosurgical device having an end effector comprising:
   first and second opposing interfacing surfaces, said interfacing surfaces capable of engaging tissue therebetween, said end effector capable of receiving bipolar energy therein;
   electrically isolated first and second poles comprising electrically opposite electrodes capable of conducting bipolar energy therethrough; and
   a stapling means for stapling tissue;
   wherein said first pole is contained on an electrically insulating portion of said first interfacing surface and said second pole is contained on said second interfacing surface so that bipolar energy may be communicated between said poles through said tissue.

2. The electrosurgical device of claim 1 wherein a portion of at least one of said first and second interfacing surfaces comprises a ridge forming a tissue compression zone between said first and second interfacing surfaces.

3. The electrosurgical device of claim 2 wherein said first and second poles are arranged to provide coagulation in the compression zone when current flows between said first and second poles.

4. The electrosurgical device of claim 2 wherein a portion of said first interfacing surface comprises a ridge forming a tissue compression zone between said interfacing surfaces and wherein a portion of said second interfacing surface comprises a ridge forming said tissue compression zone.

5. The electrosurgical device of claim 2 wherein said ridge is arranged on the second interfacing surface to compress tissue against the first pole.

6. The electrosurgical device of claim 1 wherein the first pole comprises an elongated electrode.

7. The electrosurgical device of claim 1 wherein said device is adapted to weld tissue.

8. The electrosurgical device of claim 1 further comprising a cutting element associated with said end effector, said cutting element adapted to divide tissue engaged by said end effector, through a cutting line.

9. The electrosurgical device of claim 8 wherein the end effector is adapted to provide hemostasis lateral to said cutting line.

10. The electrosurgical device of claim 8 wherein said stapling means is adapted to apply staples lateral to said cutting line.

11. The electrosurgical device of claim 8 wherein said cutting element is adapted to move in a cutting path to form said cutting line.

12. The electrosurgical device of claim 8 wherein said cutting line comprises a substantially circular shape.

13. The electrosurgical device of claim 12 wherein said first pole is relatively circular in shape and is located on an outer circumference of said first interfacing surface; and wherein said cutting line is located radially inward from said first pole.

14. The electrosurgical device of claim 1 wherein said stapling means comprises:
- a cartridge containing parallel rows of staples, having a slot extending longitudinally therethrough for a cutting means to travel between the rows of staples, said cartridge forming the second interfacing surface;
- driving means for applying staples to tissue in between the surfaces; and
- an anvil for receiving and forming said staples, said anvil forming a portion of the first interfacing surface.

15. The electrosurgical device of claim 14 wherein said driving means applies staples to tissue as the cutting means cuts between the parallel rows.

16. The electrosurgical device of claim 14 wherein bipolar energy is applied before the cutting means is advanced.

17. The electrosurgical device of claim 14 wherein each of said parallel rows of staples includes a plurality of stacked staple rows capable of being fired in succession.

18. The electrosurgical device of claim 1 wherein said stapling means is capable of being used to rejoin a lumen.

19. The electrosurgical device of claim 1 wherein said stapling means comprises:
- a cartridge containing staples arranged about an outer periphery of said cartridge;
- a cutting means for cutting tissue, said cutting means located radially inward of said staples; driving means for applying staples to tissue between said interfacing surfaces; and
- an anvil for receiving and forming said staples, said anvil forming a portion of the first interfacing surface.

20. The electrosurgical device of claim 19 wherein said driving means applies staples to tissue as said cutting means divides tissue.

21. The electrosurgical device of claim 19 wherein bipolar energy is applied prior to dividing tissue with cutting means.

22. The electrosurgical device of claim 19 wherein said cartridge includes a plurality of stacked staples capable of being fired in succession.

23. An electrosurgical device having an end effector comprising:
- first and second opposing interfacing surfaces, said interfacing surfaces capable of engaging tissue therebetween, said end effector capable of receiving bipolar energy therein,
- electrically isolated first and second poles comprising electrically opposite electrodes capable of conducting bipolar energy therethrough; and
- a stapling means for stapling tissue;
- wherein said first pole is contained on a said first interfacing surface and said second pole is contained on said second interfacing surface so that bipolar energy may be communicated between said poles through said tissue; and
- wherein at least one of said poles comprises a series of electrically communicating electrodes staggered on at least one of said first and second interfacing surfaces.

24. The electrosurgical device of claim 23 wherein said at least one pole is arranged in a parallel manner with respect to the electrically opposite pole.

25. An electrosurgical device having an end effector comprising:
- first and second opposing interfacing surfaces, said interfacing surfaces capable of engaging tissue therebetween, said end effector capable of receiving bipolar energy therein;
- electrically isolated first and second poles comprising electrically opposite electrodes capable of conducting bipolar energy therethrough; and
- a stapling means for stapling tissue;
- wherein said first pole is contained on a said first interfacing surface and said second pole is contained on said second interfacing surface so that bipolar energy may be communicated between said poles through said tissue;
- wherein said first pole comprises a series of first electrodes and said second pole comprises a series of second electrodes; and
- wherein the first electrodes alternate with said second electrodes on each of said first and second interfacing surface.

26. An electrosurgical device having an end effector comprising:
- first and second opposing interfacing surfaces, said interfacing surfaces capable of engaging tissue therebetween, said end effector capable of receiving bipolar energy therein;
- electrically isolated first and second poles comprising electrically opposite electrodes capable of conducting bipolar energy therethrough; and
- a stapling means for stapling tissue;
- a cutting means for dividing tissue through a cutting line;
- wherein said first pole is contained on a said first interfacing surface and said second pole is contained on said second interfacing surface so that bipolar energy may be communicated between said poles through said tissue; and
- wherein the first pole comprises a first and second electrode between which the cutting means is adapted to move.

27. The electrosurgical device of claim 26 wherein said first and second electrode each comprise a parallel elongated bar electrode in electrical communication, wherein said end effector further comprises a slot adapted to receive the cutting element, and wherein the cutting element is adapted to travel through the slot and between the bar electrodes.

28. An electrosurgical instrument comprising:
- a handle,
- an actuating means coupled to said handle,
- an end effector coupled to the distal end of said actuating means,
- a means for communicating bipolar electrical energy from a bipolar energy source to said end effector,
- said end effector including:
  - a first interfacing surface,
  - a second interfacing surface,
  - a first pole located on an electrically insulating portion of said first interfacing surface,
  - a second pole located on said second interfacing surface, and
  - a stapling means for stapling tissue,
- wherein said actuating means is capable of causing said end effector to engage tissue between the first interfacing surface and the second interfacing surface,
- wherein said first pole and said second pole are electrically opposite electrodes capable of conducting electrical energy supplied from said means for communicating bipolar electrical energy from a bipolar energy source, through tissue adjacent said first pole and said second pole, and
- wherein said stapling means is capable of securing tissue together.

* * * * *